US00PP28074P3

(12) United States Plant Patent
Gray et al.

(10) Patent No.: US PP28,074 P3
(45) Date of Patent: Jun. 6, 2017

(54) FLORIBUNDA ROSE PLANT NAMED 'GRAAPR'

(50) Latin Name: ***Rosa* hybrid**
Varietal Denomination: GRAapr

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 14/998,452

(22) Filed: Jan. 5, 2016

(65) Prior Publication Data

US 2016/0198603 P1 Jul. 7, 2016

(30) Foreign Application Priority Data

Jan. 7, 2015 (AU) ..... PBR 2015002

(51) Int. Cl.
*A01H 5/02* (2006.01)

(52) U.S. Cl.
USPC ..... Plt./147

(58) Field of Classification Search
USPC ..... Plt./147
CPC ..... A01H 5/0222
See application file for complete search history.

*Primary Examiner* — Kent L Bell

(57) ABSTRACT

'GRAapr' is a new and distinct floribunda type *Rosa* hybrid cultivar which is characterized by the combination of an upright to semi-weeping growth habit, complete resistance to *Diplocarpon rosae*, nearly continuous flowering, double-type apricot flowers with a strong citrus-like fragrance, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination:

The inventive variety of *Rosa* hybrid disclosed herein has been given the variety denomination 'GRAapr'.

CROSS REFERENCE TO RELATED APPLICATIONS

This application claims priority to the Australian Plant Breeder's Rights application number 2015002, filed on Jan. 7, 2015, which is herein incorporated by reference.

BACKGROUND OF THE INVENTION

The present invention relates to a new and distinct *Rosa* hybrid, floribunda rose cultivar, which has been given the variety denomination of 'GRAapr'.

Parentage: 'GRAapr' is a seedling selection which resulted from the controlled cross-pollination of an unnamed *Rosa* hybrid female breeding line and an unnamed *Rosa* hybrid male breeding line. Both parents, developed by the same inventor and never commercially released, exhibited traits deemed commercially significant and desirable.

After many years of trialing, the female parent was confirmed to possess a combination of desirable traits such as complete resistance to rose black spot disease, complete resistance to powdery mildew, and flowers with a strong citrus-like perfume borne on a bushy plant growing to 1.2 m tall and wide. The male parent was selected for use in breeding after trialing confirmed the presence of strong true-rose perfume and a bright, modern flower color. During the summer of 2010, the female parent was emasculated and was manually pollinated with pollen from the male parent. In autumn of 2010, seed was collected from hips produced by the female parent and a number of seedlings were grown to a mature size, including the claimed plant. These progeny were further evaluated for desirable traits such as black spot disease resistance and strong perfume, and in June of 2011 the claimed plant was first observed. In spring of 2013, after further evaluation for desirable traits, the claimed plant was deemed to be garden-worthy and suited to widespread cultivation. It was given the denomination, 'GRAapr'.

Asexual Reproduction: Asexual propagation of 'GRAapr', by way of softwood stem cuttings, was first performed in May of 2011 at the inventor's nursery in Highfields, Australia. Through twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAapr'. These traits, in combination, distinguish 'GRAapr' as a new and distinct cultivar.

1. *Rosa* hybrid 'GRAapr' exhibits an upright to semi-weeping growth habit; and
2. *Rosa* hybrid 'GRAapr' exhibits complete resistance to the plant pathogen, *Diplocarpon rosae*, commonly referred to as rose black spot disease; and
3. *Rosa* hybrid 'GRAapr' exhibits nearly continuous flowering; and
4. *Rosa* hybrid 'GRAapr' exhibits a double flower type; and 5. *Rosa* hybrid 'GRAapr' exhibits an apricot flower color with light pink intonations at the marginal zone and soft yellow intonations towards the base; and
6. *Rosa* hybrid 'GRAapr' exhibits flowers with a strong citrus-like fragrance.

DETAILED BOTANICAL DESCRIPTION

Figure 1:
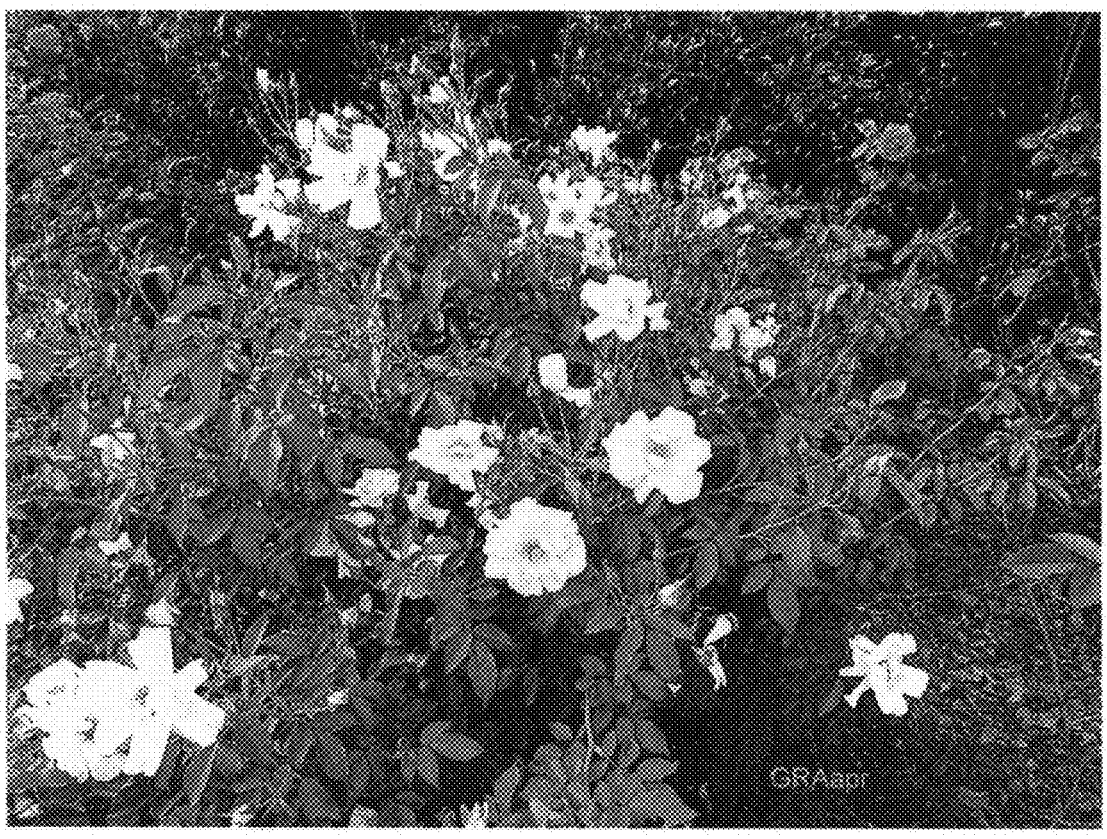
FIG. 1 illustrates, as nearly true as it is reasonably possible to make the same in color photographs of this type, an exemplary 2 year old 'GRAapr' plant grown outdoors at the inventor's commercial nursery in Highfields, Australia.
Figure 2:
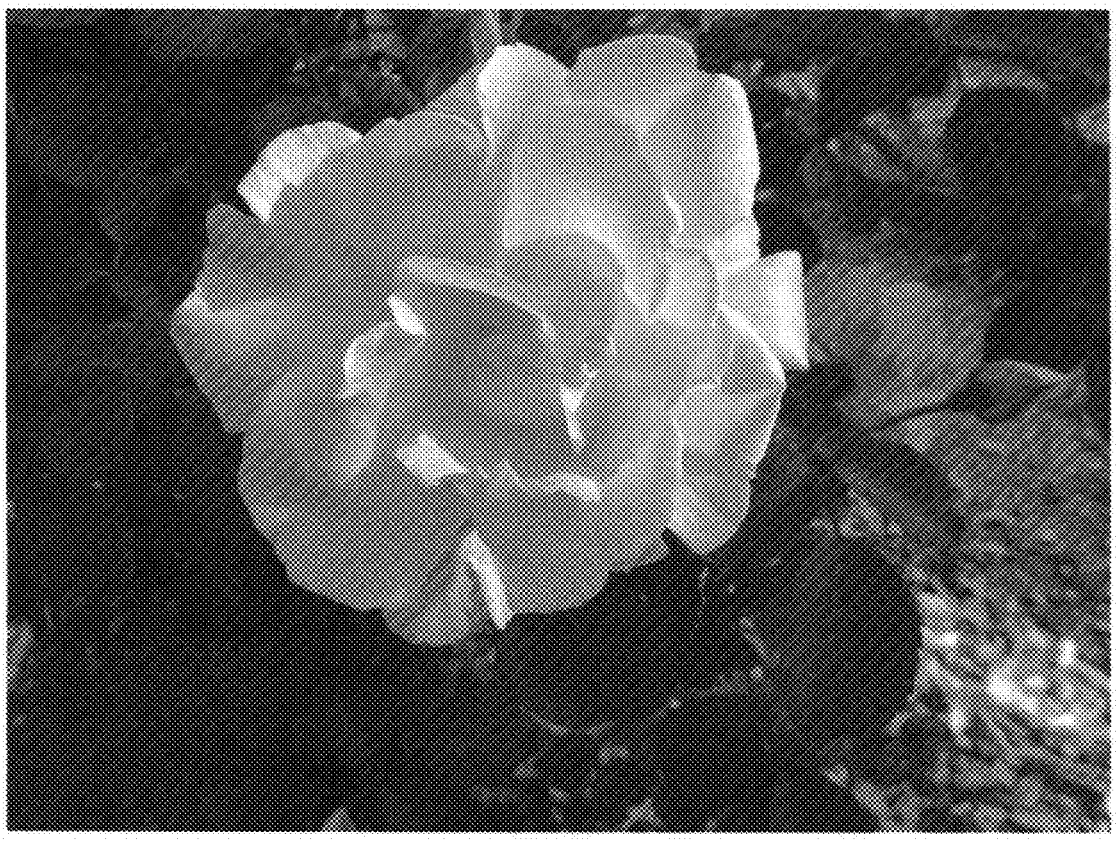
FIG. 2 illustrates, as nearly true as it is reasonably possible to make the same in color photographs of this type, the typical foliage and flower of 'GRAapr'.

The following observations and measurements, made in November of 2015, describe averages of two specimens of two year old 'GRAapr' plants grown in red krasnozem soil, in full sun, at the inventor's nursery in Highfields, Australia. Temperatures ranged from approximately 17 to 23 degrees Celsius during the day and 7 to 18 degrees Celsius at night. Standard practices for irrigation, fertilizer and pest control were applied at appropriate times during the growing season. The plants were pruned on Jul. 7, 2015 using accepted techniques for rose pruning.

Those skilled in the art will appreciate that certain characteristics will vary with older or, conversely, with younger plants. 'GRAapr' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth Edition except where common terms of color are used.

A botanical description of 'GRAapr' and comparisons with the parents and the most similar commercial cultivar of *Rosa* hybrid are provided below.

General plant description:

*Growth habit*.—Upright to semi-weeping.

*Growth rate*.—Approximately 2 years to reach 90 cm.

*Mature dimensions*.—90 cm tall and 80 cm wide.

*Cold hardiness*.—Unknown.

*Disease resistance*.—Complete resistance to powdery mildew (*Sphaerotheca pannosa*) and blackspot (*Diplocarpon rosae*).

Propagation:

*Technique*.—Softwood stem cuttings.

*Time to initiate roots*.—About 13 days at approximately 21 degrees Celsius at root zone and 18 degrees Celsius ambient temperature.

*Time to produce a rooted cutting*.—About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost four to five buds near the apex of each shoot.

*Quantity*.—Numerous.

*General dimensions*.—Approximately 70 cm long; 0.4 cm in diameter near the base and tapering to 0.2 cm.

*Immature branches*.—Diameter — Approximately 0.3 cm. Texture — Smooth; glabrous to moderately pubescent. Color — Near RHS 184A with anthocyanin intonations at and near the apex, and RHS 145B towards the base. Prickles — Density — Few to moderately dense. Color — Near RHS 34B. Shape — Concave. Texture — Smooth.

*Mature branches*.—Diameter — Approximately 1 cm, after 2 years. Texture — Smooth; glabrous. Color — Near RHS 143C. Prickles — Density — Medium. Color — Near RHS 42B. Shape — Concave. Texture — Smooth.

Leaves:

*Arrangement*.—Opposite imparipinnate compound leaves.

*Attachment*.—Petiolate.

*Dimensions*.—12 cm long and 8 cm wide, on average.

*Petiole*.—Dimensions — Average of 1.5 to 2.2 cm long and 0.2 cm wide. Color — Near RHS 148D. Texture — Glabrous to lightly pubescent with few small hairs. Prickles — Not present. Stipitate glands — Not present.

*Stipule*.—Dimensions — 1.2 cm long and 0.6 cm wide. Color — Near RHS 148D. Texture — Glabrous to lightly pubescent with few small hairs. Margins — Ciliate. Apex — Acuminate. Base — Fused to the petiole. Prickles — Present. Stipitate glands — Not present.

*Rachis*.—Dimensions — 1.7 cm long and 0.2 cm wide. Color — Near 135D. Prickles — Present. Stipitate glands — Not present.

*Leaflets*.—Quantity — Normally 7 leaflets on axillary leaves. Dimensions — Average size of the terminal leaflet is 45 mm long and 27 mm wide. Shape — Ovate. Apex — Acuminate. Base — Ovate. Margins — Serrated. Texture, pubescence and luster, adaxial surface — Smooth, glabrous, and semi-glossy. Texture, pubescence and luster, abaxial surface — Smooth, glabrous, and matte. Juvenile foliage color, adaxial surface — Near RHS 139B. Juvenile foliage color, abaxial surface — Near RHS 147D. Mature foliage color, adaxial surface — Near RHS 139B. Mature foliage color, abaxial surface — Near RHS 141D. Venation — Reticulate. Venation color, adaxial surface — Near RHS 139A. Venation color, abaxial surface — Near RHS 147B.

*Petiolule*.—Dimensions — 0.2 cm long and 0.1 cm wide. Color — Near RHS 67A. Prickles — Not present. Texture — Smooth.

Inflorescence:

*Inflorescence type*.—Terminal corymb consisting of four to seven pedicellate flowers.

*Blooming habit*.—Almost continuous from October through June in the southern hemisphere.

*Time to flower*.—6 to 8 weeks for a new stem to mature and flowering begins to occur once a stem matures.

*Dimensions*.—8.5 cm from the base of the base of the lowest pedicel to the farthest distal flower and 19 cm from farthest outstretched flower on one side of the inflorescence to the farthest outstretched flower on the opposite side.

*Peduncle*.—Dimensions — 2.5 to 3.0 cm long and 0.2 cm in diameter. Color — Near RHS 134D. Strength — Strong. Texture — Smooth.

Bud:

*Bud form*.—Ovate.

*Size*.—2 cm long and 1 cm in diameter.

*Color*.—Near RHS 143D.

Flower:

*Pedicel*.—Dimensions — 1.5 to 3.4 cm long and 0.2 cm wide. Color — Near RHS 134D. Strength — Strong. Texture — Smooth.

*Calyx*.—General — Comprised of five polysepalous sepals, with two to three weak foliaceous appendages. Diameter of calyx — 0.5 cm.

*Sepals*.—Color, interior surface — RHS 149D. Color, exterior surface — RHS 143D. Dimensions — 2 cm long and 0.6 cm wide. Apex — Acuminate. Base — Flat at union with receptacle. Quantity — Five. Texture — Densely puberulent. Margins — Two to three weak foliaceous appendages. Stipitate glands — Not present.

*Corolla*.—General shape of corolla — Double; irregularly round. Rate of opening — 6 days from bud to anthesis. Dimensions — 7 cm in diameter and 3.5 cm deep. Fragrance — Strong citrus-like scent. Lastingness — On the plant for 5 days after anthesis. Persistence — Self-cleaning.

*Petals*.—Petal count — Exhibits double flowers with approximately 18 petals under normal conditions. Petal arrangement — Loose, irregular whorl. Petal reflex — Slightly reflexed. Petal margin — Entire; slightly undulating. Petal shape — Obovate. Apex — Rounded to cordate. Base — Flattened, then obtuse. Dimensions — 3.6 cm long and 2.8 cm wide. Texture — Soft.

*Petal color, upon opening*.—Upper surface — Near RHS 28C. Lower surface — Near RHS 16C.

*Petal color, at anthesis*.—Upper surface — Near RHS 23C. Lower surface — Near RHS 12C. Fading — Apricot general tonality and tinged with light pink, near RHS 55C, at the marginal zone and soft yellow, near RHS 12B, towards the base.

Reproductive organs:

*Stamens*.—Quantity — Approximately 50.

*Anthers*.—Shape — Narrow ovate. Length — 0.2 cm. Color — Near RHS 21B. Pollen — Many. Pollen Color — Near RHS 3A.

*Filaments*.—Color — Near RHS 9A. Length — 0.7 cm.

*Pistils*.—Quantity — Approximately 50. Length — Approximately 1 cm.

*Stigmas*.—Shape — Ovate. Color — Near RHS 11B.

*Styles*.—Length — Approximately 0.8 cm long. Color — Near RHS 158C.

*Ovary*.—Dimensions — 0.5 cm long and 0.3 cm wide. Color — Near RHS 3D.

*Receptacle*.—Shape — Pitcher-shaped. Dimensions — 0.5 cm high and 0.5 cm wide. Color — Near RHS 147D.

Hip and seed:

*Hip*.—Shape — Rounded. Dimensions — 1 cm long and 1 cm wide. Texture — Smooth. Color — Near RHS 138C.

*Seed*.—Quantity — One to four. Shape — Rounded. Dimensions — 1 cm high and 1 cm wide. Color — Near RHS 134D.

COMPARISONS WITH THE PARENTS

The new rose plant 'GRAapr' may be distinguished from its seed parent, an unnamed breeding line, by the following combination of characteristics:

1. The flowers of 'GRAapr' exhibit an apricot general tonality with tinges of light pink at the marginal zone and tinges of soft yellow towards the base, whereas the flowers of the seed parent exhibit a solid light pink general tonality.
2. 'GRAapr' exhibits an upright to semi-weeping growth habit, whereas the seed parent exhibits an upright growth habit.

The new rose plant 'GRAapr' may be distinguished from its pollen parent, an unnamed breeding line, by the following combination of characteristics:

1. The flowers of 'GRAapr' exhibit an apricot general tonality with tinges of light pink at the marginal zone and tinges of soft yellow towards the base, whereas the flowers of the pollen parent exhibit a solid purple general tonality.
2. 'GRAapr' exhibits an upright to semi-weeping growth habit, whereas the pollen parent exhibits an upright growth habit.

COMPARISONS WITH THE MOST SIMILAR VARIETY OF COMMON KNOWLEDGE

Plants of the new cultivar 'GRAapr' may be distinguished from the commercial variety *Rosa* hybrid 'GRAsuper' (U.S. Plant Pat. No. 23,175) by the following combination of characteristics:

1. The flowers of 'GRAapr' exhibit an apricot general tonality with tinges of light pink towards the apex and tinges of soft yellow towards the base, whereas the flowers of 'GRAsuper' exhibit a solid light pink general tonality.
2. 'GRAapr' exhibits a petal count of approximately 18 petals, whereas 'GRAsuper' typically possesses 46 petals.
3. 'GRAapr' exhibits a rachis length of 1.7 cm, whereas 'GRAsuper' exhibits a rachis length of 2.5 cm.
4. The adaxial surface of the juvenile foliage of 'GRAapr' is colored near RHS 139B, whereas the adaxial surface of the juvenile surface of 'GRAsuper' is colored near RHS 137C.

That which is claimed:

1. A new and distinct variety of *Rosa* hybrid plant named 'GRAapr', as described and illustrated herein.

* * * * *